US006913590B2

(12) United States Patent  
Sorenson et al.

(10) Patent No.: US 6,913,590 B2
(45) Date of Patent: Jul. 5, 2005

(54) APPARATUS AND METHOD FOR PERITONEAL DIALYSIS

(75) Inventors: James LeVoy Sorenson, Salt Lake City, UT (US); LeVoy G. Haight, West Jordan, UT (US); Frank McNeil, Sandy, UT (US); Gloria Smith, Salt Lake City, UT (US); Reed F. Winterton, Salt Lake City, UT (US)

(73) Assignee: Sorenson Development, Inc., Salt Lake City, UT (US)

( * ) Notice: Subject to any disclaimer, the term of this patent is extended or adjusted under 35 U.S.C. 154(b) by 0 days.

(21) Appl. No.: 09/962,027

(22) Filed: Sep. 24, 2001

(65) Prior Publication Data

US 2002/0123715 A1 Sep. 5, 2002

(Under 37 CFR 1.47)

Related U.S. Application Data

(60) Provisional application No. 60/234,681, filed on Sep. 22, 2000.

(51) Int. Cl.$^7$ .......................... A61M 1/00; A61M 5/00; A61N 1/30; N01B 1/00
(52) U.S. Cl. .......................... 604/29; 604/174; 604/19; 604/27; 210/645
(58) Field of Search .......................... 604/20–27, 254, 604/19, 175, 249, 6.09, 29, 30, 31, 36, 307, 308, 113, 5.04, 6.11, 158, 252, 284, 44, 126, 8, 518, 4.01; 210/739, 252, 646, 85, 87, 140, 241; 600/16, 485, 486; 366/132.2, 160.2, 167.1, 174.1; 514/12

(56) References Cited

U.S. PATENT DOCUMENTS 4,560,472 A * 12/1985 Granzow et al. ........... 210/140
6,074,359 A *  6/2000 Keshaviah et al. ........... 604/29
6,409,699 B1 *  6/2002 Ash ........................... 604/29

FOREIGN PATENT DOCUMENTS

WO        WO 0103754      *  1/2001

* cited by examiner

*Primary Examiner*—Nicholas D. Lucchesi
*Assistant Examiner*—Roz Maiorino
(74) *Attorney, Agent, or Firm*—TraskBritt

(57) ABSTRACT

An apparatus and method for treatment of end stage renal decline and failure through peritoneal dialysis enabling ambulatory transfer of dialysate to and from the peritoneum of a renal patient, this in synthesis and coordination with normal physiological rhythms of the patient. The system remains unobtrusive and less restrictive of patient ambulation and orientation. The present invention includes expendables disposability of which facilitates safe reuse of more expensive portions and is sufficiently simple for use in a home care environment. It may be designed to incorporate real-time, interactive or remote monitoring and regulation and visual or audible indication of system pressures, chemical balances and other important variables.

76 Claims, 6 Drawing Sheets

APPARATUS AND METHOD FOR PERITONEAL DIALYSIS

PRIORITY CLAIM

This application claims the priority benefit of Provisional Patent Application Ser. No. 60/234,681, filed Sep. 22, 2000, for "APPARATUS AND METHOD FOR PERITONEAL DIALYSIS."

BACKGROUND OF THE INVENTION

1. Field of the Invention

This invention relates to means for treatment of renal decline and failure. It is particularly directed to an improved system for ambulatory transfer of dialysate to and from the peritoneum.

2. State of the Art

Medical practice has numerous applications for treatment of impaired renal function and ultimate decline and failure with peritoneal dialysis. The application of peritoneal dialysis, involves introduction of a dialysate solution to the peritoneal cavity outside the omentum, through an indwelling single lumen catheter entering the peritoneum through the abdominal wall near the pelvis. The dialysate remains within the peritoneum for approximately four hours until osmotic diffusion of bodily wastes from a renal patient through the semipermeable epithelial tissues approaches an equilibrium of saturation in the dialysate. At some point within this terminal range of approach the dialysate is functionally exhausted and is transferred out of the peritoneum and exchanged for a new infusion of unused dialysate.

Existing peritoneal dialysis systems suffer from any of a number of disadvantages. Most devices require the patient to be tethered and confined and to be situated at a fixed location with a dializing bag hanging from an IV stand for gravity feed throughout the transfer of dialysate to and from the peritoneum of the patient and do not permit ambulation during transfer of dialysate. Some systems utilize pumps that have the disadvantages of substantial cost, size and weight that are prohibitive of significant ambulation during dialysate transfer.

Irrespective of which paradigm has been used, heretofore, peritoneal dialysis procedures presuppose introduction and maintenance of a total of approximately three liters or twelve pounds of dialysate solution to and within the peritoneum for an extended period of time for the patient, with the epithelial tissues of the peritoneum acting essentially as an artificial kidney; the process uncomfortably expands and distends the abdomen of the patient and results in discomfort, disfigurement, flatulence and inconvenience. These disadvantages are virtually continuous from the inception of each dialysis treatment.

Prior art devices for containment of dialysate bags for gravity flow have heretofore been available exclusively for attachment to IV stands adjacent to the patient's person, precluding comfort in movement such as standing, walking or other ambulation and other positions and activities and, further also, detracting from the aesthetic appeal to the patient and diminishment of the patient's body balance and self-image.

Previous peritoneal dialysis processes only crudely infer the terminal range within which dialysate has approached equilibrium, is exhausted and to be exchanged for unused dialysate. The inference is drawn from historic norms of a broad population despite potentially substantial variances from one individual to another.

A related disadvantage of prior art peritoneal dialysis is the deleterious effect on surrounding epithelial tissues from extended exposure to dialysate that is saturated with caustic bodily toxins. Upon diagnosis of end stage renal failure, the present prognosis is between two and three years life expectancy, due in large measure to the continuous unnaturally high exposure of these sensitive tissues to noxious bodily wastes within exhausted dialysate.

Heretofore, inefficiencies have resulted from infusion of excessive or insufficient amounts of dialysate relative to the needs of the particular patient during a particular time frame. Similarly, dialysate infused in ideal amounts but incorrectly presumed to be exhausted is occasionally discarded prematurely.

There is a need for a dialysis system providing ambulatory, unobtrusive, light weight, symmetric, orientation-neutral and convenient storage and containment of new or exhausted dialysate and associated systems.

A further need exists for such a renal treatment system with single patient components that are inexpensive, disposable and sufficiently simple for use in a home care or ambulatory environment.

There remains a need for an improved peritoneal dialysis system wherein electronic circuitry and associated indicators enable monitoring of the solute and regulation of flow rates, including system pressures, temperature, system timing, chemical balances and other therapeutic variables to more closely mimic and optimize normal physiological patterns and to enhance the patient's and physician's ability to determine optimal dosage, regime and protocol to obtain such goals.

There exists a need for such monitoring and regulation optionally from locations remote from the patient. Whether remote or not, there is a continuing need for the foregoing features that may be actuated automatically or by direct intervention based on real time interaction.

Further yet, there is a need for a peritoneal dialysis system closely customized to the circumstances of a particular patient enabling a more accurate determination of the terminal point at which exhausted dialysate is to be reconditioned or transferred from the patient and exchanged for unused dialysate or, if practicable, reconditioned dialysate.

SUMMARY OF THE INVENTION

The present invention provides an improved apparatus and method for ambulatory patient dialysis including transfer of peritoneal dialysate and comprising monitoring, regulation and indication of therapeutic variables to more closely parallel the natural, pre-symptomatic kidney function and excretion patterns of the renal system and to achieve correspondent acceptable physiological function.

This novel system enables coordination of fluid transfers and dialysis processes with ambient physiological activity of the patient. Balance in physiological dynamics is enhanced with a more effective delivery and monitoring system that follows natural rhythms. A system of indicators may communicate various therapeutic variables and physiological measurements, for example, urea, presence of air, temperatures and electrolytes in the dialysate. Accordingly, the indicator system results in reduction of incidence of peritonitis, potentially resulting in cost savings and because it is more efficient in determining the parameters of the dialysate thereby improving timing and fluid exchange. Such fine tuning of physiological balances enhances the physician's and patient's ability to determine optimal dynamic dosage, regime and protocol for the benefit of the patient, irrespective of physical orientation of the patient or of the treatment system or of both. The system entails a small portable pump, filter system, receptacle, with improvements comprising a dialyzing fluid bag designed to be worn, which may alternatively simply be hung from an IV stand for gravity flow where preferably, a novel vest for low profile, aesthetically appealing, symmetric and unobtrusive system containment and placement, and indicators whereby fluid flow rates, volume, timing, direction, pulsating patterns and dialysate and bodily electrolytes, urea, protein, acid-base balances as examples may be monitored and regulated. The system comprising these improvements is inexpensive, disposable and sufficiently simple for use in a home care environment and may be equipped with a real-time monitor and indicator of various system conditions, dialysate parameters and other important therapeutic variables.

The invention in one embodiment is a device system for treatment of and support during renal decline or failure. It comprises a portable pump including a disposable cartridge interface; a receptacle system, which may be bladder-like, comprising exhausted dialysate storage capacity and unused or recycled dialysate storage capacity, designed selectively to be worn by a patient; a conduit which may be structured and arranged to support passage of unused or recycled dialysate to and exhausted dialysate from a peritoneum of the patient and a filter assembly associated with the conduit and structured and arranged to permit filtering of both air and contaminants from the unused or recycled dialysate.

The receptacle system may include a polymer bag with a first wall and an opposing second wall, and include at least one opening in fluid communication with the conduit. It further may include structure attached to an inner side of the first wall and to an opposing inner side of the second wall to retain the cross-sectional dimension of the bag within a limited range of distention of the bag when a dialysate is in the bag without limiting flow of the dialysate in or through the bag. Alternatively, for the same purpose, the receptacle system may include either a dimensionally stable or a semi-rigid encasement structured and arranged to abut the bag against at least one of the walls. The encasement may comprise a single plate in combination with a vest or a pocket.

The patient vest of the present invention, where utilized, may be structured and arranged to support the receptacle system proximal to and with minimal cross-sectional extension from the patient. The vest may be configured to support the receptacle system irrespective of location, orientation or movement of the patient. It comprises any of at least two sides which may include a front side, back side, left side and right side. It further comprises means of affixing the vest in close proximity to the body of said patient such as, alone or in combination, any of either Velcro® or buckles or straps or button structure with corresponding eye structure or ties or zipper or belt or at least one hole through which an arm of a patient may be placed. A pocket or pouch is associated with at least one of the sides whereby at least a portion of the receptacle system may be enveloped within the pocket or pouch.

Indicator means may also be included whereby at least one therapeutic variable, but potentially any of a plurality of therapeutic or diagnostic variables, may be monitored or regulated to determine and establish optimal dynamic dosage or optimal dynamic regime or optimal dynamic protocol, or any of all of the foregoing. Such optimal dynamics enable achievement of a desired therapeutic balance. The indicator means may further enable detection of achievement of the desired therapeutic balance. Such therapeutic variables may be monitored or regulated selectively automatically or by direct intervention and may be monitored or regulated from a source remote from the patient. These therapeutic variables may comprise, alone or in combination, dialysate temperature or dialysate flow volume or dialysate flow direction or dialysate flow timing or dialysate chemistry including, for example, albumen, urea, uric acid, creatinine, creatine, pH, ions or electrolytes. The therapeutic variables may be monitored or regulated with detection structure positioned in any of a variety of locations including without limitation associated with the conduit or the pump or the receptacle system or any combination of the foregoing. The detection structure may be located proximal to or within the body of the patient and thus may further monitor and regulate the variables of body temperature or residual pressure or blood content of the patient.

In another embodiment, the conduit of the present invention may comprise a plurality of lumens, a first of which lumens is structured and arranged to support passage of exhausted dialysate from a peritoneum of the patient, and a second of which lumens is structured and arranged to support passage of unused or recycled dialysate to the peritoneum. A third lumen may be structured and arranged to measure directly or by inference parameters such as temperature, pH and electrolytes in the peritoneum, including probes for the measurement of appropriate chemistry, pH and temperature. The system thereby enables exhausted dialysate to be admitted and unused or recycled dialysate to be delivered in alternating sequence or simultaneously in reciprocating circulation. In this embodiment the first lumen includes a corresponding first distal orifice, and the second lumen includes a corresponding second distal orifice. The first and second distal orifices may be located within the peritoneum at respective sites remote from each other. Subject to determination by an attending physician, the point of entry of the conduit may generally preferably be through the abdomen, near the pelvis or alternatively, particularly in cases involving reciprocal circulation or recycling of dialysate, at a point near but below the diaphragm. The passage of dialysate may be in the form of any of a variety of pulsating flow patterns, and may be coordinated to increase rate, frequency and magnitude of dialysate circulation along, against and among epithelial and other tissues of and within the peritoneum. Thus, exhausted dialysate may be admitted and unused or recycled dialysate may be delivered simultaneously.

Accordingly, the present invention contemplates a method of performing peritoneal dialysis, comprising selection of the above characterized device system for treatment of renal decline or failure; association of said device system with an indwelling dialysis catheter such that substantially all of an amount of exhausted dialysate within a peritoneum of a patient may be removed to be disposed of or processed for recycling; and infusion of a therapeutic volume of unused or recycled dialysate optimal for treatment of the patient.

In accordance with this method a selected volume of unused dialysate, which is in excess of the therapeutic volume and is sufficient to accomplish dialysis through an extended period of time during which the patient may be in a sleeping condition, may selectively be introduced to the peritoneum of the patient. This method may incorporate the distention-limiting structure within or around the receptacle system, may accommodate simultaneous or sequential passage or reciprocal circulation of exhausted and unused or recycled dialysate, either of which may be in a pulsating flow pattern, and may involve having the exhausted dialysate undergo a process that extends its useful life such as, alone or in combination, filtration or chemical, electrical, thermal or light modification.

Likewise the conduit of this method may include a plurality of lumens, the first of which comprises a corresponding first distal orifice and is structured and arranged to permit passage of exhausted dialysate from the peritoneum and a second of which comprises a corresponding second distal orifice and permits passage of unused or recycled dialysate to the peritoneum. In this method, the first distal orifice may be located within the peritoneum at a site remote from the second distal orifice.

The therapeutic variables of this method may likewise comprise, alone or in combination, body temperature or blood content of the patient or dialysate temperature or dialysate flow volume or dialysate flow direction or dialysate flow timing or dialysate chemistry balance including albumen, urea, uric acid, creatinine, creatine, pH, ions or electrolytes and may be monitored or regulated selectively automatically or by direct intervention, which may be from a source remote from the patient.

The device system of this method may further comprise the aforementioned patient vest structured and arranged to support the receptacle system proximal to and with minimal cross-sectional extension from the patient, which method may be performed irrespective of the location, physical orientation or movement of the patient.

This device system and method may utilize any of a variety of indicators and associated structures, alone or in combination, such as chemical, electrical or light based technologies, including chemiluminescent, biofluorescent, electrochemical and chemical color indicators.

BRIEF DESCRIPTION OF THE SEVERAL VIEWS OF THE DRAWINGS

In the drawings, which illustrate what is currently regarded as the best mode for carrying out the invention.

DETAILED DESCRIPTION OF THE ILLUSTRATED EMBODIMENTS

Figure 1:
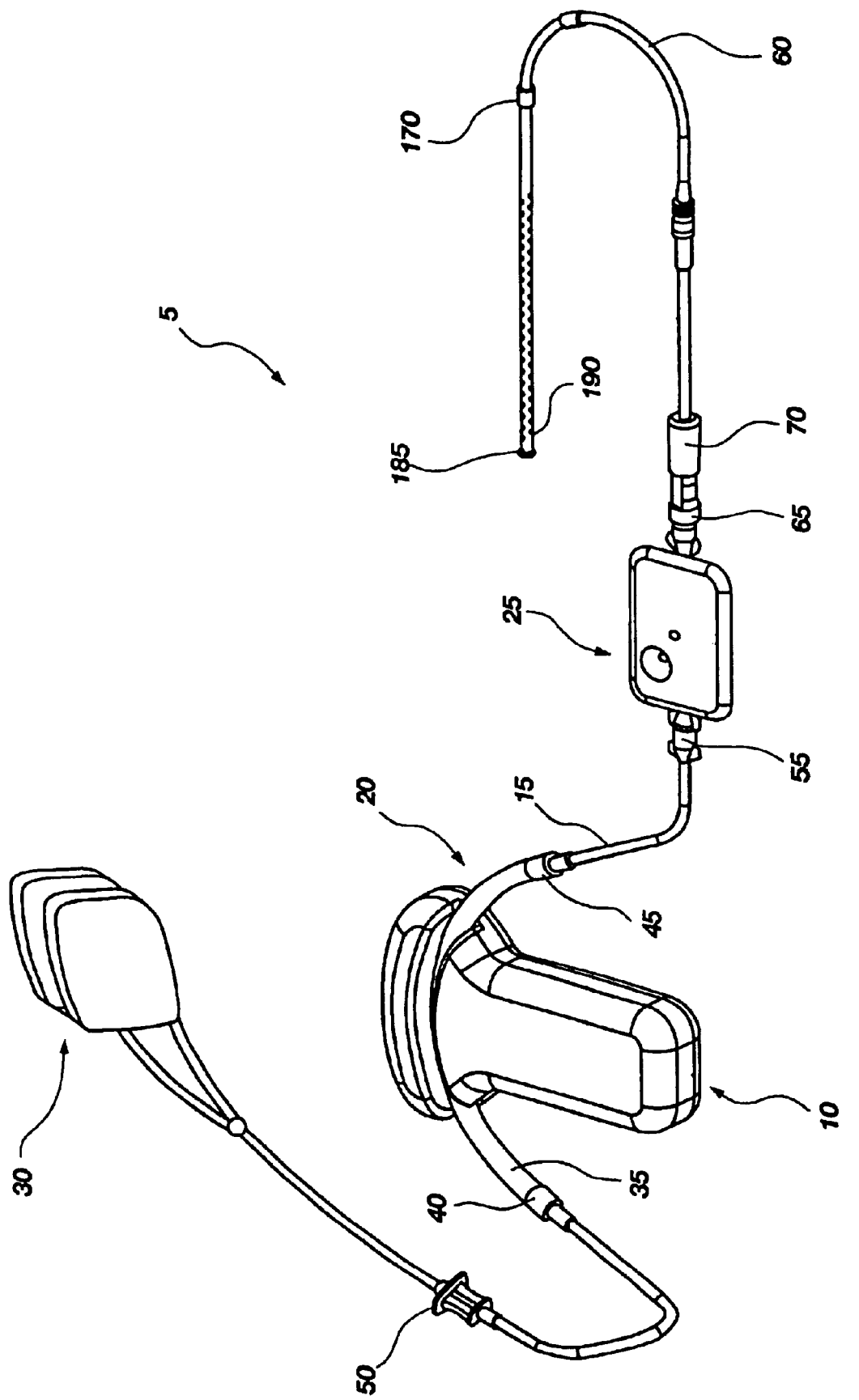
FIG. 1 is a perspective view of the preferred embodiment of the device system.

The structural elements of one configuration of the present novel device system 5 for peritoneal dialysis are shown in FIG. 1. A pump 10 is detachably associated with a flexible conduit 15, preferably having cross-sectional patency, along a disposable cartridge interface 20 between a filter 25 and a receptacle system 30.

The illustrated pump 10 operates on the basis of peristaltic action but other pump mechanisms not illustrated could be utilized for portable, high-volume operation. The cartridge 20 comprises collapsible, resilient tubing 35 and is in fluid communication with the conduit 15 by means of couplings 40, 45. The conduit 15 may be releasibly associated in fluid communication with the receptacle system 30 at a junction 50 and with the filter 25 at a joint 55. The filter 25 is releasibly coupled to and in fluid communication with an indwelling catheter 60 at a patient disconnect 65. An indicator means 70 may be placed at any of a variety of locations, alone or in combination, depending upon the nature of the indicator means and its function or functions, as further elaborated below, but is depicted as being located between the catheter 60 and the filter 25.

Figure 2A:
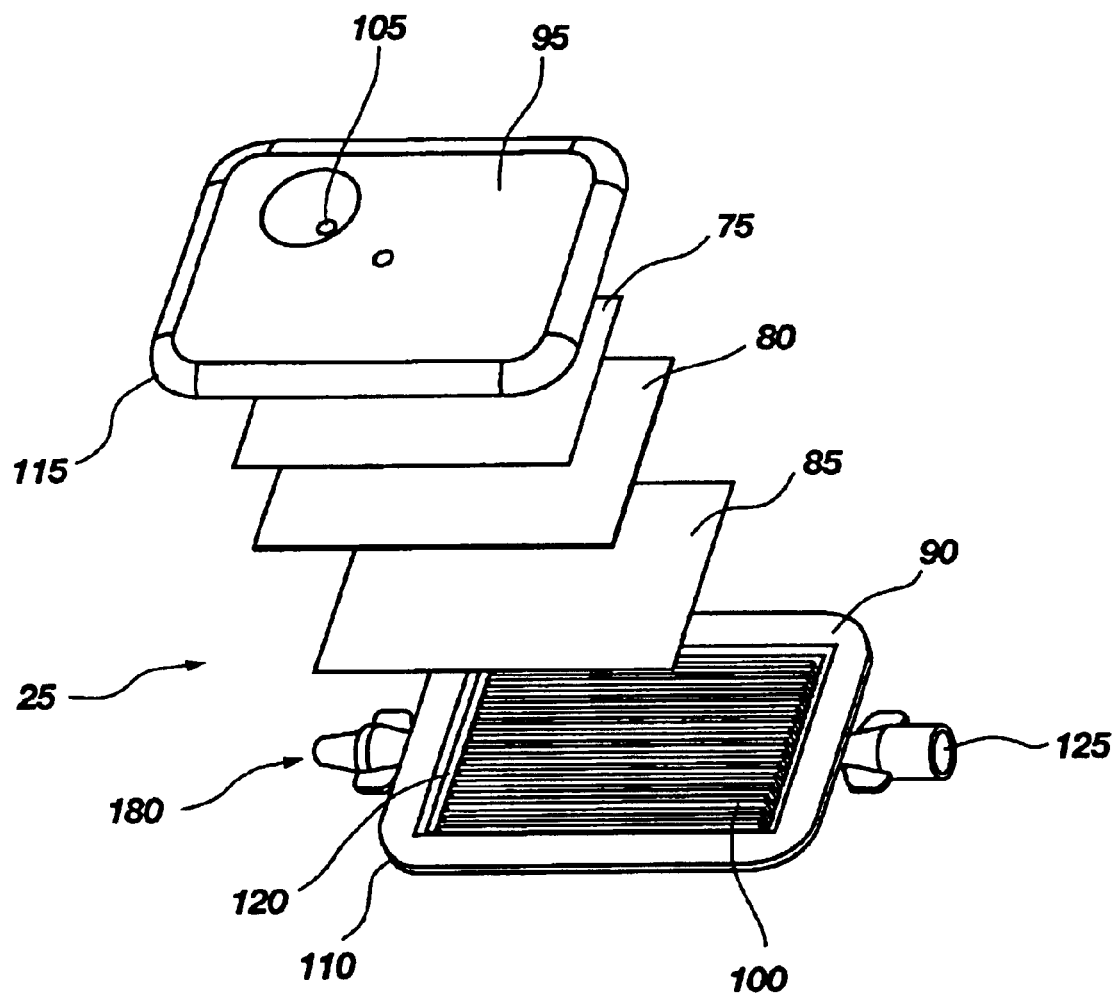
FIG. 2 is a partially exploded view of the filter.

More particularly set forth in FIG. 2a, the filter 25 comprises a hydrophobic filter 75, a hydrophilic screen 80 and a hydrophilic filter 85 all sequenced between a base 90 and a convex capture lid 95. The base 90 includes internal ribs 100 which abut and support the hydrophilic filter 85 while accommodating exposure of maximum surface area of the hydrophilic filter 85 to dialysate throughput. The hydrophilic screen 80 provides counter support for the hydrophilic filter 85 and support for the hydrophobic filter 75. The convex curvature of the capture lid 95 accommodates the hydrophobic filter 75 and passage of air therethrough. The lid 95 includes an air outlet 105 for air screened from passing dialysate by the hydrophobic filter 75. The base 90 and lid 95 are sealed together along their respective periphery 110,115 by any commercially feasible means such as, for example, a press-fit, sonic weld or adhesive.

Dialysate passage toward the peritoneum through the filter 25 is accommodated through an upstream port 120 that admits dialysate to the filter 25 between the hydrophobic filter 75 and hydrophilic filter 85. The hydrophobic filter 75 allows passage of air through to the air outlet 105 while preventing leakage of dialysate out of or penetration of contaminants into the dialysate. The hydrophilic filler 85 permits passage of the dialysate while filtering out microbial and other contaminants from the dialysate prior to its passage through a downstream port 125 and eventual entrance into the peritoneum.

Figure 2B:
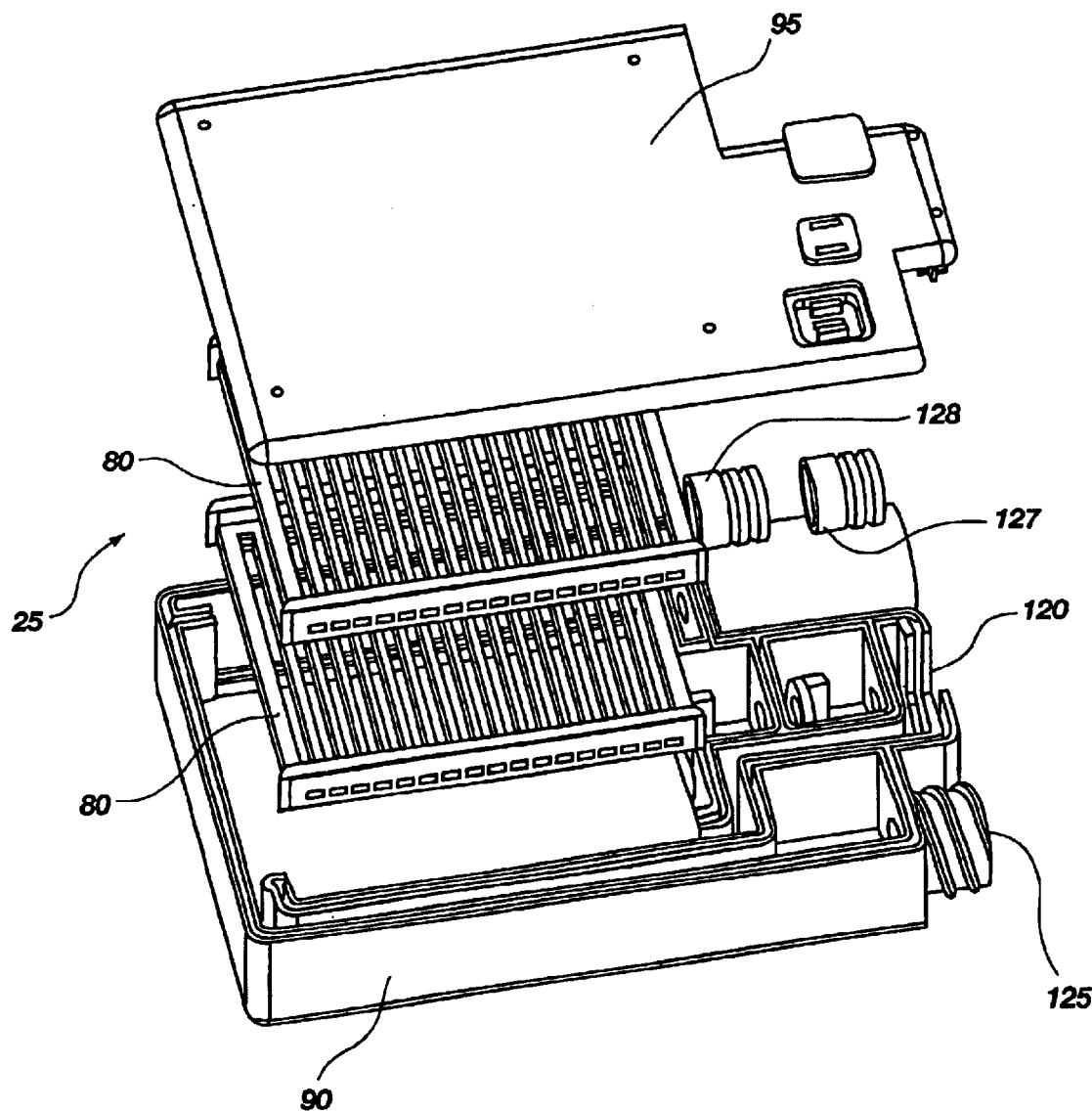

As illustrated in FIG. 2b, exhausted dialysate passing out of the peritoneum can, depending on the configuration of the filter 25, either pass back through the downstream port 125 and bypass the hydrophilic filter through an up stream check valve 127 associated with the upstream port 120 or entirely circumvent the filter 25 through a combination of alternate conduit and associated check valves (not shown).

Figure 3A:
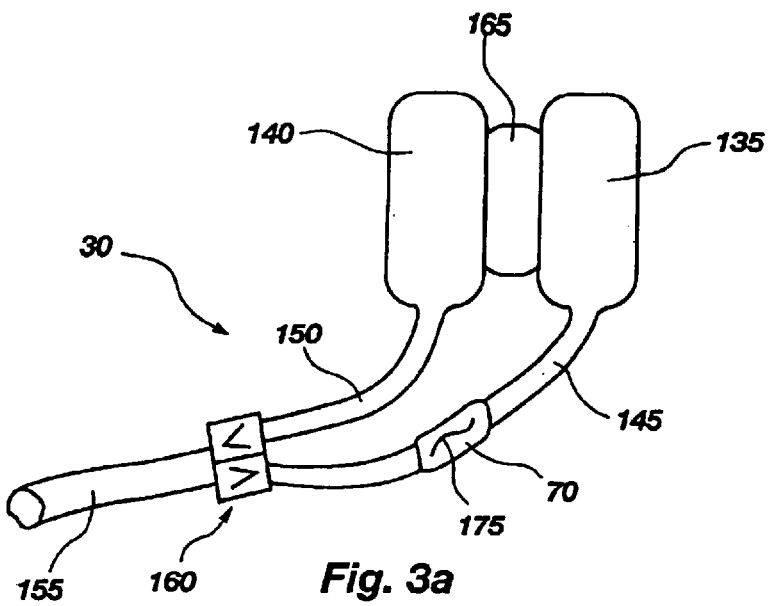
FIG. 3a is a perspective view of a first embodiment of the receptacle.
Figure 3B:
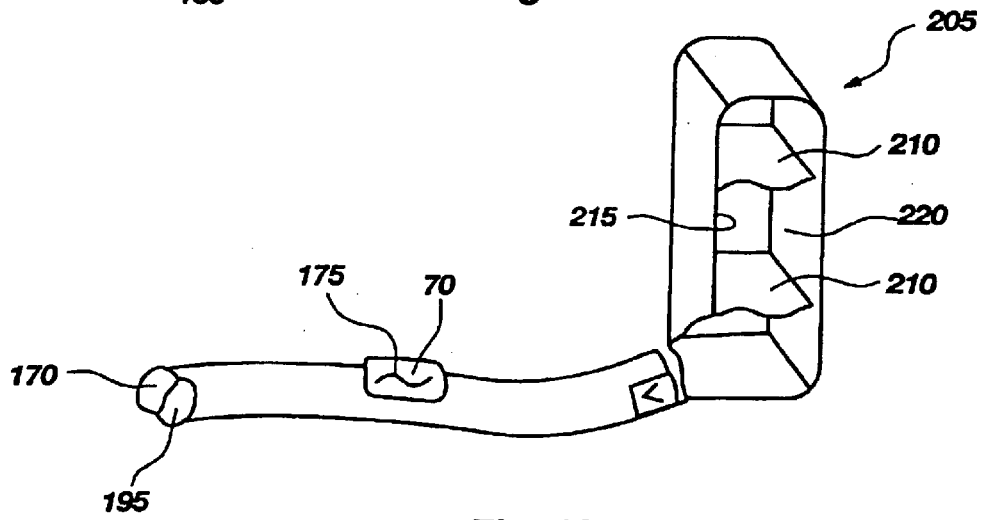
FIG. 3b is a perspective view of a partially cut away second embodiment of the receptacle.
Figure 3C:
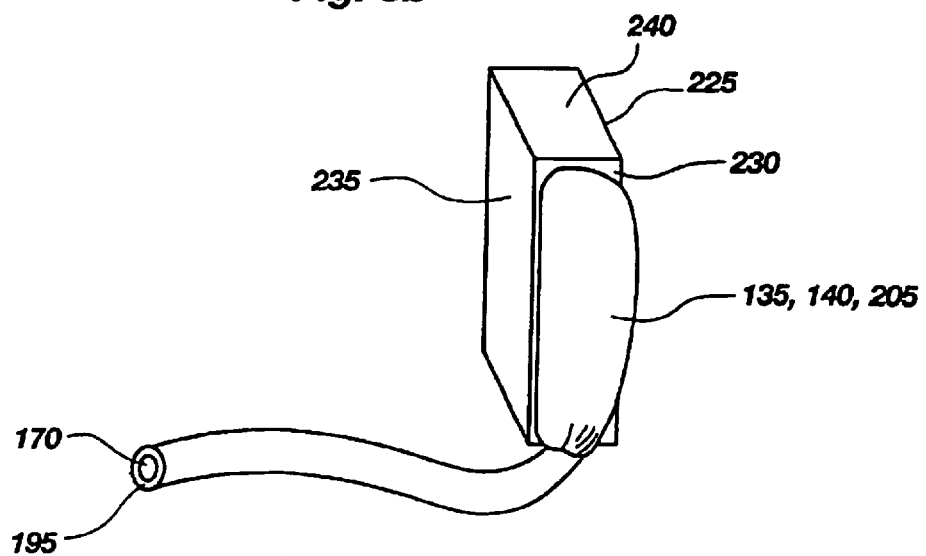
FIG. 3c is a perspective view of a partially cut away third embodiment of the receptacle.

Various configurations of the receptacle system 30 are illustrated in FIGS. 3a–3c. FIG. 3a depicts a dual bag system 30 including a disposal reservoir 135, a supply reservoir 140 and respective disposal tubing 145 and supply tubing 150 each associated with a common tubing 155 through a generally indicated check valve 160. The reservoirs 135,140 may in one configuration be connected in fluid communication with each other by a processing stage 165.

The processing stage 165 may have the capacity, alone or in combination, to filter, chemically neutralize, electronically alter or modify the condition of dialysate by other means such as, for example, with light, or heat (not shown) in a reconditioning manner. Accordingly, unused dialysate or reconditioned dialysate or a combination of both may be reintroduced to the peritoneum for additional dialysis until an appropriate level of exhaustion of the dialysate is reached.

Indicator means 70 may be associated with the device system 5 to enable regulation or monitoring or both regulation and monitoring of at least one therapeutic variable but potentially any of a plurality of therapeutic variables of the patient. Thus the present invention dramatically enhances the ability to monitor and affect key variables, e.g., to recognize decline in the condition of the peritoneal lining and its ability to participate adequately in the dialyzing process; to identify shifts in the optimal amount of residual dialysate; to ascertain changes to be made in the composition of the dialysate to be used; and to queue alterations to the frequency of transfers and exchanges.

As illustrated in FIGS. 3a and 3b, the indicator means 70 may be embodied as an electrochemical device interposed along the disposal tubing 145 or disposal lumen 170 or otherwise may comprise an indwelling electrode 175 in fluid communication with the dialysate. The electrode 175 may be structured and arranged to provide on-line, real-time, objective, quantitative information about the status of the dialysate. The electrode 175 may further be associated with transmission means or receiver means or transceiver means or regulator means or monitor means (none of which is shown) enabling communication to or from a monitor or regulator or both a monitor and regulator (not shown) which monitor or regulator may be remote from the device system 5. Examples of such probes include pH probes available from Omega Engineering, Inc. of Stamford, Conn. and pH conductivity probes from The Hach Company of Loveland, Colo. Non-electrical, chemical pH probes may similarly be utilized. Examples of such electrochemical probes include the ammonia $NH_4$ probe of Omega Engineering, Inc., or seven-analyte-capable probes of Yellow Springs Instruments, Yellow Springs, Ohio.

Illustrative of various applications of pH probes, the filter or tubing may include a pH strip in contact with used dialysate that responds to the alkaline nature of the urine content of used dialysate. The pH level is directly proportional to the concentration of alkaline waste (comprised mostly of urea); a higher pH level would indicate that the used dialysate comprises a higher concentration of waste products. To preclude leaching from the indicator to the new or reconditioned dialysate to be infused into the peritoneum, the probe may be positioned between the upstream check valve 127 and downstream check valve 128 within the filter 25. An example of one group of compounds that could be used as an indicator is anthrocyanins or quinones. A slight modification of this configuration involves use of the pH indicator material on the surface of the material molded as a system component that is in fluid communication with the used dialysate. Similarly, the pH material may be integral with such molding material. Thus the used dialysate causes pH indicator material exposed on the component surface and in fluid communication with the used dialysate to change color. This change may be detected by a sensor (not shown) to determine waste product concentration. Indicators for other waste products may also be used. As an alternative to the pH indicator, material that changes color in response to exposure to other waste products could be utilized.

Alternatively, indicator means 70 may be embodied as a chemical test involving a color strip indicator (not shown) exposed to a sample of dialysate removed from the peritoneum, preferably from the upstream side 180 of the filter 25 so as to limit the potential for peritonitis. The color strip changes color in direct relation to the extent to which the dialysate approaches the osmotic diffusion equilibrium. For example, a new color strip colored red may become colored mauve when exposed to slightly used dialysate or purple with moderately used dialysate, but become colored blue when fully exhausted. Accordingly a patient or care giver is enabled to recognize more accurately when dialysate has arrived at the optimal dynamic terminal point, and thus is informed that an infusion of new or reconditioned dialysate is needed. For example, QuantiMetrix Corp. of Redondo Beach, Calif. or Diagnostic Chemicals, Ltd. of Prince Edward Island, Canada with its U.S. subsidiary supplies impregnated paper indicator materials used with colorimetry dipsticks or other impregnated materials capable of such colormetrics functions.

Yet another embodiment of the indicator means 70 is in the nature of modified electrochemical or chemiluminescence tests wherein a sensor is associated with a selected site of the skin of a renal patient (net shown) and an electronic current is introduced to stimulate dilation of pores and thereby enable access to the subcutaneous interstitial tissues with selected light waves. The reflective and refractive interaction between the light wave lengths and the liquids of which the interstitial tissues are comprised enables a determination of constituents of the liquids. Comparison of the constituents with the known relationship between waste products in blood and interstitial liquids enables an inference of the proximity to the terminal point on the dialysis rate curve. Materials supportive of such an embodiment are available through Diagnostic Chemicals, Ltd. U.S.A. of Oxford, Conn.

Another embodiment of an indicator may utilize a wavelength of light that is absorbed or otherwise affected by a certain waste chemical. An LED (not shown) may be structured and arranged to shine a light though the tubing as well as the used dialysate as it flows through the tubing. An associated sensor (not shown) detects the amount or nature of light that passes through the fluid. The amount or nature of light reflected or attenuated by the used dialysate is relative to the concentration of waste chemical in the used dialysate and accordingly provides an indication of the condition of the used dialysate.

Additional indicator means may be embodied as a probe 185 associated with remote tip 190 of the indwelling catheter 60, for measuring temperature, pressure, blood characteristics or the like.

FIG. 3b illustrates one configuration of the receptacle system 30 involving a dual lumen alternative, including the disposal lumen 170 and a supply lumen 195. A supply check valve 200 may be interposed on the supply lumen 195 in configurations involving a single bag reservoir 205 where both lumens 170, 195 pass through the cartridge interface 20 of the pump 10 instead of parting to allow the disposal lumen to circumvent the pump.

Retaining structure 210 may be attached to opposing inner sides 215, 220 of a bag 135, 140, 205 to retain the cross-sectional dimension of the bag 135, 140, 205 within a limited range of distention, and thus to enhance the comfort, mobility and appearance of the patient when the device system 5 is being carried or worn, during either dialysis or ambulatory transfer.

Alternative retention structure illustrated in FIG. 3c involves a dimensionally stable or a semi-rigid encasement 225 that compresses the dialysate bag 205 or bags 135, 140 between a first side 230 and second side 235 connected to each other by at least one connecting member 240.

Figure 4A:
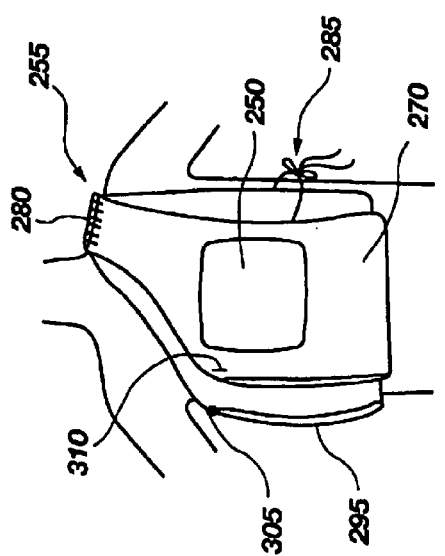
FIG. 4a depicts a perspective view of a first embodiment of the vest of the system relative to the patient.
Figure 4B:
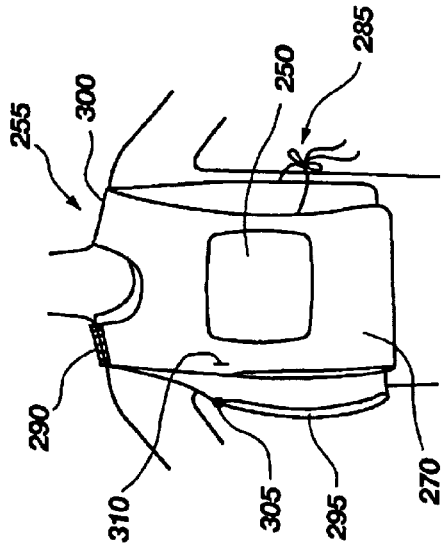
FIG. 4b depicts a perspective view of a second embodiment of the vest of the system.
Figure 4C:
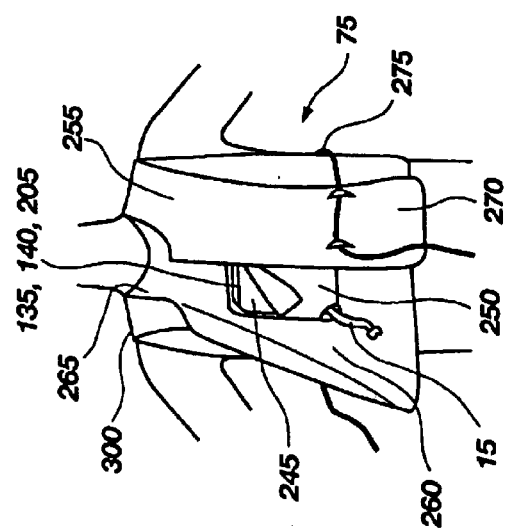
FIG. 4c depicts a perspective view of a third embodiment of the vest of the system.
Figure 4D:
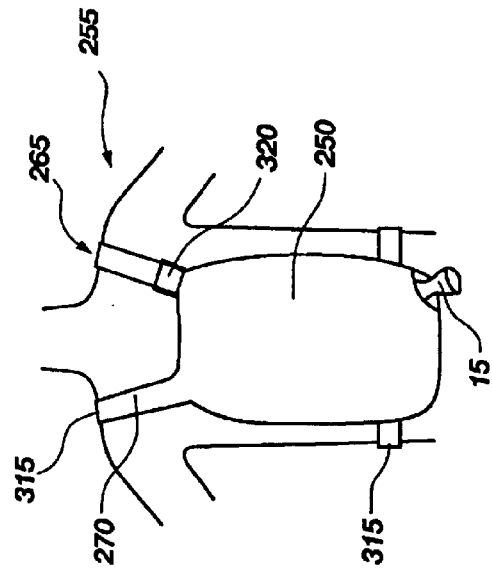
FIG. 4d depicts a perspective view of a fourth embodiment of the vest of the system.

Yet another retention structure illustrated in FIG. 4c is a dimensionally stable or a semi-rigid plate 245 within a pocket 250 of a vest 255 in a manner that limits the distention of the bag 205 or bags 135, 140 and thereby retains the cross-sectional dimension of the receptacle system 30 at a minimum.

The nature, location and function of the indicator means 70 and receptacle system 30 to be selected for use with the device system 5 is influenced at least by the particular function to be accomplished or variable or variables sought to be indicated. It will be appreciated that a wide variety of potential permutations of the features of the receptacle system 30 or indicator means 70 may be adapted to a preferred embodiment in accordance with the preferences or needs of a given patient or service provider or circumstance. Accordingly, specific illustration of the nature, location or function of indicator means 70 or receptacle system 30 in the present disclosure should not be understood to limit the intended scope of the appended claims.

For containment of the portable device system 5, any of a variety of vest configurations is contemplated in the present invention as partially set forth generally in FIGS. 4a–4d. FIG. 4c illustrates one preferred embodiment of the vest 255 that is structured and arranged in a configuration to contain the device system 5 within the pocket 250. The pocket 250 is located on the inside 260 of the back side 265 of the vest 255. In this configuration the vest 255 opens up from the front side 270.

The vest 255 may be configured to position the pocket 250 on the front side 270 as well, as set forth in FIGS. 4a and 4b, or on a left side or right side (not shown). Similarly, the vest 255 depicted in FIG. 4d resembles a daypack; accordingly, the pocket 250 comprises a substantial portion of the vest and may be worn on the front side 270 or back side 265 of the patient.

Similar versatility may be embodied in the means of attaching the vest 255 to the patient. Belts 275, laces 280 including ties 285, zippers 290, Velcro® 295, sewn seams 300, buttons 305 with eyes 310, straps 315, buckles 320 and any other such means of connecting may be utilized.

Figures 5A, 5B:
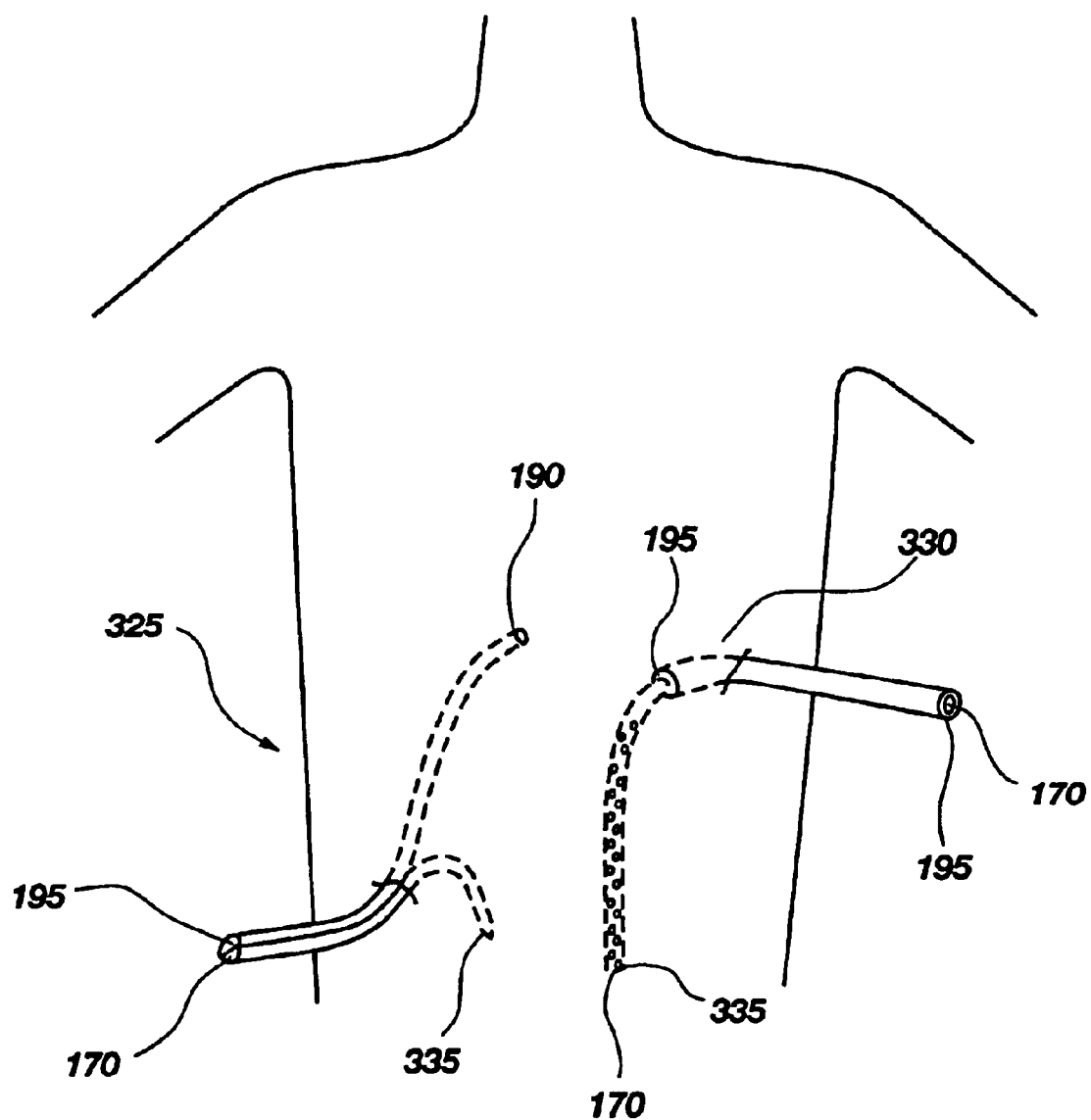
FIG. 5a illustrates an adjacent dual lumen structure comprising remote distal tips.
FIG. 5b similarly portrays a concentric dual lumen structure including remote distal tips.

In FIGS. 5a and 5b, one advantageous aspect of a multi-lumen feature is illustrated. Whether the plurality of lumens is in a side by side configuration as illustrated in FIG. 5a or concentric as illustrated in FIG. 5b, and irrespective of the location of the insertion site of the catheter 60, the remote tip 190 of the supply lumen 195 can be located within the peritoneal cavity 325 at an infusion site 330 that enhances the washing action of the unused or reconditioned dialysate across the omentum within the peritoneal cavity. For an ambulatory patient, for example, such a site 330 would be just below the diaphragm. In such an application, the tip 190 is preferably remote from the terminal end 335 of the disposal lumen 170; for example, the terminal end 335 would be located in the lower abdominal area near the pelvis.

The device system and method of the present invention provide distinct advantages over prior peritoneal dialysis systems and methods. Thus, reference herein to specific details of the illustrated or other preferred embodiments is by way of example and not intended to limit the scope of the appended claims. It will be apparent to those skilled in the art that many modifications of the basic illustrated embodiments may be made without departing from the spirit and scope of the invention as recited by the claims.

What is claimed is:

1. A device system for treatment of and support during renal decline or failure, comprising:
   a portable pump including a disposable cartridge interface;
   a receptacle system comprising exhausted dialysate storage capacity and unused or recycled dialysate storage capacity, designed selectively to be worn by a patient;
   a conduit structured and arranged to support passage of unused or recycled dialysate to and exhausted dialysate from a peritoneum of the patient;
   a filter assembly associated with the conduit and structured and arranged to permit filtering of both air and contaminants from unused or recycled dialysate; and
   indicator means whereby at least one physiological, therapeutic or diagnostic variable but potentially any of a plurality of variables may be monitored or regulated to determine and establish any or all of an optimal dynamic dosage or optimal dynamic regime or optimal dynamic protocol, thereby to achieve a desired therapeutic balance.
   wherein said conduit structured and arranged to support passage of unused or recycled dialysate to and exhausted dialysate from a peritoneum of the patient comprises a disposal tube connected to said exhausted dialysate storage capacity, and a supply tube connected to said unused or recycled dialysate storage capacity, said disposal tube and supply tube in connection with a common tube through a check.

2. The system of claim 1, wherein said indicator means enables detection of achievement of the desired therapeutic balance.

3. The system of claim 1, wherein said variables may be monitored or regulated selectively automatically or by direct intervention.

4. The system of claim 1, wherein said variables may be monitored or regulated from a source remote from the patient.

5. The system of claim 1, wherein said variables may comprise, alone or in combination, dialysate temperature or dialysate flow volume or dialysate flow direction or dialysate flow timing or dialysate chemistry balance including albumen, urea, uric acid, creatinine, creatine, pH, ions or electrolytes.

6. The system of claim 5, wherein said variables may further comprise body temperature, residual pressure or blood content of the patient and be monitored or regulated with detection structure located proximal or within the body of the patient.

7. The system of claim 5, wherein said variables may be monitored or regulated with detection structure associated with the conduit.

8. The system of claim 5, wherein said variables may be monitored or regulated with detection structure associated with the pump.

9. The system of claim 5, wherein said variables may be monitored or regulated with detection structure associated with the receptacle system.

10. The system of claim 1, wherein the conduit comprises a plurality of lumens, a first of which lumens is structured and arranged to support passage of exhausted dialysate from a peritoneum of the patient, and a second of which lumens is structured and arranged to support passage of unused or recycled dialysate to the peritoneum.

11. The system of claim 10, wherein said exhausted dialysate is admitted and said unused or recycled dialysate is delivered in alternating sequence.

12. The system of claim 10, wherein the first of which lumens comprises a corresponding first distal orifice, and the second of which lumens comprises a corresponding second distal orifice, wherein said first and second distal orifices may be located within the peritoneum at respective sites remote from each other.

13. The system of claim 10, wherein said passage of dialysate may be in the form of a pulsating flow.

14. The system of claim 13, wherein said pulsating flow through the first and second distal orifices may be coordinated to increase dialysate circulation within the peritoneum.

15. The system of claim 10, wherein said exhausted dialysate is admitted and said unused or recycled dialysate is delivered simultaneously.

16. The system of claim 1, wherein said receptacle system comprises a polymer bag comprising a first wall and an opposing second wall, and includes at least one opening in fluid communication with said conduit.

17. The system of claim 1, wherein said receptacle system includes structure attached to an inner side of the first wall and to an opposing inner side of the second wall to retain the cross-sectional dimension of the bag within a limited range of distention of the bag when a dialysate is in the bag without limiting flow of the dialysate therein or therethrough.

18. The system of claim 1, wherein said receptacle system includes a dimensionally stable or a semi-rigid encasement structured and arranged to abut the bag against at least one of said walls to retain the cross-sectional dimension of the bag within a limited range of distention of the bag when a dialysate is in the bag without limiting flow of the dialysate therein or therethrough.

19. The system of claim 18, wherein said encasement comprises a single plate in combination with a patient vest.

20. The system of claim 18, wherein said encasement comprises a single plate in combination with a pocket.

21. The system of claim 19, wherein said patient vest comprises any of at least two sides which may include a front side, back side, left side and right side.

22. A device system for treatment and support during renal decline or failure, comprising:
a portable pump including a disposable cartridge interface;
a receptacle system comprising exhausted dialysate storage capacity and unused or recycled dialysate storage capacity, designed selectively to be worn by a patient;
a conduit;
a filter assembly associated with the delivery conduit and structured and arranged to permit filtering of both air and contaminants from unused or recycled dialysate;
wherein the conduit comprises a plurality of lumens, a first of which lumens is structured and arranged to support passage of exhaused dialysate from a peritoneum of the patient, and a second of which lumens is structured and arranged to support passage of unused or recycled dialysate to the peritoneum.

23. The system of claim 22, wherein said exhausted dialysate is admitted and said unused or recycled dialysate is delivered in alternating sequence.

24. The system of claim 22, wherein the first of which lumens comprises a corresponding first distal orifice, and the second of which lumens comprises a corresponding second distal orifice, wherein said first and second distal orifices may be located within the peritoneum at respective sites remote from each other.

25. The system of claim 22, wherein said passage of dialysate may be in the form of a pulsating flow.

26. The system of claim 25, wherein said pulsating flow through the first and second distal orifices may be coordinated to increase rate, frequency and magnitude of dialysate circulation along, against and among epithelial and other tissues of and within the peritoneum.

27. The system of claim 22, wherein said exhausted dialysate is admitted and said unused or recycled dialysate is delivered simultaneously.

28. The system of claim 22, further comprising indicator means whereby at least one but potentially any of a plurality of therapeutic variables may be monitored or regulated to determine and establish any or all of an optimal dynamic dosage or optimal dynamic regime or optimal dynamic protocol, thereby to achieve a desired therapeutic balance.

29. The system of claim 28, wherein said therapeutic variables may be monitored or regulated with detection structure associated with the conduit.

30. The system of claim 28, wherein said therapeutic variables may further comprise body temperature or blood content of the patient and be monitored or regulated with detection structure located within the body of the patient.

31. The system of claim 22, wherein said receptacle system comprises a polymer bag comprising a first wall and an opposing second wall, and includes at least one opening in fluid communication with said conduit.

32. The system of claim 22, wherein said receptacle system includes structure attached to an inner side of the first wall and to an opposing inner side of the second wall to retain the cross-sectional dimension of the bag within a limited range of distention of the bag when a dialysate is in the bag without limiting flow of the dialysate therein or therethrough.

33. The system of claim 22, wherein said receptacle system includes a dimensionally stable or a semi-rigid encasement structured and arranged to abut the bag against at least one of said walls to retain the cross-sectional dimension of the bag within a limited range of distention of the bag when a dialysate is in the bag without limiting flow of the dialysate therein or therethrough.

34. The system of claim 33, wherein said encasement comprises a single plate in combination with a patient vest.

35. The system of claim 33, wherein said encasement comprises a single plate in combination with a pocket.

36. The system of claim 34, wherein said patient vest comprises any of at least two sides which may include a front side, back side, left side and right side.

37. A device system for treatment and support during renal decline or failure, comprising:
a portable pump including a disposable cartridge interface;
a receptacle system comprising exhausted dialysate storage capacity and unused or recycled dialysate storage capacity, designed selectively to be worn by a patient;
a conduit structured and arranged to support passage of unused or recycled dialysate to and exhausted dialysate from a peritoneum of the patient;
a filter assembly associated with the delivery conduit and structured and arranged to permit filtering of both air and contaminants from unused or recycled dialysate; and
a patient vest structured and arranged to support the receptacle system proximal to and with minimal cross-sectional extension from the patient.

38. The system of claim 37, wherein said vest may be configured to support said receptacle system irrespective of location, orientation or movement of the patient.

39. The system of claim 37, wherein said receptacle system comprises a polymer bag comprising a first wall and an opposing second wall, and includes at least one opening in fluid communication with said conduit.

40. The system of claim 37, wherein said receptacle system includes structure attached to an inner side of the first wall and to an opposing inner side of the second wall to retain the cross-sectional dimension of the bag within a limited range of distention of the bag when a dialysate is in the bag without limiting flow of the dialysate therein or therethrough.

41. The system of claim 37, wherein said receptacle system includes a dimensionally stable or a semi-rigid encasement structured and arranged to abut the bag against at least one of said walls to retain the cross-sectional dimension of the bag within a limited range of distention of the bag when a dialysate is in the bag without limiting flow of the dialysate therein or therethrough.

42. The system of claim 41, wherein said encasement comprises a single plate in combination with the vest.

43. The system of claim 41, wherein said encasement comprises a single plate in combination with a pocket.

44. The system of claim 37, wherein said patient vest comprises any of at least two sides which may include a front side, back side, left side and right side.

45. The system of claim 44, wherein said patient vest further comprises means of affixing the vest in close proximity to the body of said patient.

46. The system of claim 45, wherein said affixing means comprise, alone or in combination, any of either Velcro® or buckles or straps or button structure with corresponding eye structure or ties or zipper or belt or at least one hole through which an arm of a patient may be placed.

47. The system of claim 44, wherein a pouch is associated with at least one of said sides whereby at least a portion of said receptacle system may be enveloped within the pouch.

48. The system of claim 37, further comprising indicator means whereby at least one therapeutic variable but potentially any of a plurality of therapeutic variables may be monitored or regulated to determine and establish any or all of an optimal dynamic dosage or optimal dynamic regime or optimal dynamic protocol, thereby to achieve a desired therapeutic balance.

49. The system of claim 37, wherein said indicator means enables detection of achievement of the desired therapeutic balance.

50. The system of claim 37, wherein said therapeutic variables may be monitored or regulated selectively automatically or by direct intervention.

51. The system of claim 37, wherein said therapeutic variables may be monitored or regulated from a source remote from the patient.

52. The system of claim 37, wherein said therapeutic variables may comprise, alone or in combination, dialysate temperature or dialysate flow volume or dialysate flow direction or dialysate flow timing or dialysate chemistry balance including albumen, urea, uric acid, creatinine, creatine, pH, ions or electrolytes.

53. The system of claim 52, wherein said therapeutic variables may further comprise body temperature, residual pressure or blood content of the patient and be monitored or regulated with detection structure located proximal or within the body of the patient.

54. The system of claim 52, wherein said therapeutic variables may be monitored or regulated with detection structure associated with the conduit.

55. The system of claim 52, wherein said therapeutic variables may be monitored or regulated with detection structure associated with the pump.

56. The system of claim 52, wherein said therapeutic variables may be monitored or regulated with detection structure associated with the receptacle system.

57. A device system for treatment of and support during renal decline or failure, comprising:

a portable pump including a disposable cartridge interface;
a receptacle system comprising exhausted dialysate storage capacity and unused or recycled
dialysate storage capacity, designed selectively to be worn by a patient; a conduit structured and arranged to support passage of unused or recycled dialysate to and
exhausted dialysate from a peritoneum of the patient; a filter assembly associated with the conduit and structured and arranged to permit filtering of
both air and contaminants from unused or recycled dialysate; and indicator means whereby at least one physiological, therapeutic or diagnostic variable but potentially any of a plurality of variables may be monitored or regulated to determine and establish any or all of an optimal dynamic dosage or optimal dynamic regime or optimal dynamic protocol, thereby to achieve a desired therapeutic balance, wherein said conduit structured and arranged to support passage of unused or recycled dialysate to and exhausted dialysate from a peritoneum of the patient comprises a disposal tube connected to said exhausted dialysate storage capacity, and a supply tube connected to said unused or recycled dialysate storage capacity, said disposal tube and supply tube in connection with a common tube through a check valve.

58. The system of claim 57, wherein said exhausted dialysate storage capacity and said unused or recycled dialysate storage capacity are in fluid communication through a processing stage.

59. The system of claim 58, wherein said processing stage is configured to recondition the dialysate.

60. The system of claim 59, wherein said processing stage is configured to recondition said dialysate by filtration, chemical neutralization, or electronic alteration.

61. The system of claim 59, wherein said processing stage is configured to recondition said lysate using light or heat.

62. The system of claim 57, wherein said indicator means enables detection of achievement of the desired therapeutic balance.

63. The system of claim 57, wherein said variables may be monitored or regulated selectively automatically or by direct intervention.

64. The system of claim 57, wherein said variables may be monitored or regulated from a source remote from the patient.

65. The system of claim 57, wherein said variables may comprise, alone or in combination, dialysate temperature or dialysate flow volume or dialysate flow direction or dialysate flow timing or dialysate chemistry balance including albumen, urea, uric acid, creatinine, creatine, pH, ions or electrolytes.

66. The system of claim 65, wherein said variables may further comprise body temperature, residual pressure or blood content of the patient and be monitored or regulated with detection structure located proximal or within the body of the patient.

67. The system of claim 65, wherein said variables may be monitored or regulated with detection structure associated with the conduit.

68. The system of claim 65, wherein said variables may be monitored or regulated with detection structure associated with the pump.

69. The system of claim 65, wherein said variables may be monitored or regulated with detection structure associated with the receptacle system.

70. The system of claim 57, wherein the conduit comprises a plurality of lumens, a first of which lumens is structured and arranged to support passage of exhausted dialysate from a peritoneum of the patient, and a second of which lumens is structured and arranged to support passage of unused or recycled dialysate to the peritoneum.

71. The system of claim 70, wherein said exhausted dialysate is admitted and said unused or recycled dialysate is delivered in alternating sequence.

72. The system of claim 70, wherein the first of which lumens comprises a corresponding first distal orifice, and the second of which lumens comprises a corresponding second distal orifice, wherein said first and second distal orifices may be located within the peritoneum at respective sites remote from each other.

73. The system of claim 70, wherein said passage of dialysate may be in the form of a pulsating flow.

74. The system of claim 73, wherein said pulsating flow through the first and second distal orifices may be coordinated to increase dialysate circulation within the peritoneum.

75. The system of claim 70, wherein said exhausted dialysate is admitted and said unused or recycled dialysate is delivered simultaneously.

76. The system of claim 57, wherein said receptacle system comprises a polymer bag comprising a first wall and an opposing second wall, and includes at least one opening in fluid communication with said conduit.

* * * * *